(12) United States Patent
Eberle et al.

(10) Patent No.: US 7,881,573 B2
(45) Date of Patent: Feb. 1, 2011

(54) OPTICAL IMAGING PROBE CONNECTOR

(75) Inventors: Michael J. Eberle, Fair Oaks, CA (US);
Kenneth N. Bates, Beaverton, OR (US);
William W. Morey, Northridge, CA (US)

(73) Assignee: Vascular Imaging Corporation, Rancho Cordova, CA (US)

( * ) Notice: Subject to any disclaimer, the term of this patent is extended or adjusted under 35 U.S.C. 154(b) by 0 days.

(21) Appl. No.: 12/572,511

(22) Filed: Oct. 2, 2009

(65) Prior Publication Data

US 2010/0014810 A1    Jan. 21, 2010

Related U.S. Application Data

(63) Continuation of application No. 11/285,499, filed on Nov. 22, 2005, now Pat. No. 7,599,588.

(51) Int. Cl.
*G02B 6/26* (2006.01)
*C23C 16/00* (2006.01)
*A61B 5/05* (2006.01)

(52) U.S. Cl. .............................. 385/39; 385/33; 385/34; 385/35; 385/36; 385/37; 385/40; 385/41; 385/42; 385/43; 385/44; 385/45; 385/46; 385/47; 385/48; 385/73; 385/78; 385/88; 385/89; 385/90; 385/115; 118/715; 600/411

(58) Field of Classification Search ............. 385/33–37, 385/40–48, 73, 78, 88–90, 115; 118/715; 600/411
See application file for complete search history.

(56) References Cited

U.S. PATENT DOCUMENTS 4,076,379 A    2/1978   Chouinard
4,473,065 A    9/1984   Bates
4,522,193 A    6/1985   Bates (Continued)

FOREIGN PATENT DOCUMENTS

CA    2472877    7/2003

(Continued)

OTHER PUBLICATIONS

"U.S. Appl. No. 09/623,248, Notice of Allowance mailed Jun. 2, 2003", 10 pgs.

(Continued)

*Primary Examiner*—Brian M. Healy
*Assistant Examiner*—Guy G Anderson
(74) *Attorney, Agent, or Firm*—Schwegman, Lundberg & Woessner, P.A.

(57) ABSTRACT

This document discusses, among other things, a connector for an optical imaging probe that includes one or more optical fibers communicating light along the catheter. The device may use multiple sections for simpler manufacturing and ease of assembly during a medical procedure. Light energy to and from a distal minimally-invasive portion of the probe is coupled by the connector to external diagnostic or analytical instrumentation through an external instrumentation lead. Certain examples provide a self-aligning two-section optical catheter with beveled ends, which is formed by separating an optical cable assembly. Techniques for improving light coupling include using a lens between instrumentation lead and probe portions. Techniques for improving the mechanical alignment of a multi-optical fiber catheter include using a stop or a guide.

21 Claims, 8 Drawing Sheets

U.S. PATENT DOCUMENTS

| | | | |
|---|---|---|---|
| 4,587,972 A | 5/1986 | Morantte, Jr. | |
| 4,900,921 A | 2/1990 | Spillman, Jr. | |
| 4,917,097 A | 4/1990 | Proudian et al. | |
| 4,946,238 A * | 8/1990 | Sashin et al. | 385/116 |
| 5,007,705 A | 4/1991 | Morey et al. | |
| 5,070,882 A | 12/1991 | Bui et al. | |
| 5,095,911 A | 3/1992 | Pomeranz | |
| 5,099,090 A | 3/1992 | Allan et al. | |
| 5,109,463 A * | 4/1992 | Lee | 385/123 |
| 5,135,486 A | 8/1992 | Eberle et al. | |
| 5,156,772 A | 10/1992 | Allan | |
| 5,167,233 A | 12/1992 | Eberle et al. | |
| 5,183,048 A | 2/1993 | Eberle | |
| 5,186,177 A | 2/1993 | O'Donnell et al. | |
| 5,226,847 A | 7/1993 | Thomas, III et al. | |
| 5,240,004 A | 8/1993 | Walinsky et al. | |
| 5,254,112 A | 10/1993 | Sinofsky et al. | |
| 5,290,275 A | 3/1994 | Kittrell et al. | |
| 5,305,758 A | 4/1994 | Dietz et al. | |
| 5,368,037 A | 11/1994 | Eberle et al. | |
| 5,383,467 A | 1/1995 | Auer et al. | |
| 5,400,788 A | 3/1995 | Dias et al. | |
| 5,427,107 A | 6/1995 | Milo et al. | |
| 5,439,000 A | 8/1995 | Gunderson et al. | |
| 5,453,575 A | 9/1995 | O'Donnell et al. | |
| 5,486,170 A | 1/1996 | Winston et al. | |
| 5,558,669 A | 9/1996 | Reynard | |
| 5,582,171 A | 12/1996 | Chornenky et al. | |
| 5,601,087 A | 2/1997 | Gunderson et al. | |
| 5,603,327 A | 2/1997 | Eberle et al. | |
| 5,615,675 A | 4/1997 | O'Donnell et al. | |
| 5,660,180 A | 8/1997 | Malinowski et al. | |
| 5,675,674 A | 10/1997 | Weis | |
| 5,680,489 A | 10/1997 | Kersey | |
| 5,682,897 A | 11/1997 | Pomeranz | |
| 5,684,297 A | 11/1997 | Tardy et al. | |
| 5,704,361 A | 1/1998 | Seward et al. | |
| 5,718,226 A | 2/1998 | Riza | |
| 5,732,046 A | 3/1998 | O'Donnell et al. | |
| 5,748,564 A | 5/1998 | Pattanayak | |
| 5,779,643 A | 7/1998 | Lum et al. | |
| 5,779,644 A | 7/1998 | Eberle et al. | |
| 5,830,145 A | 11/1998 | Tenhoff | |
| 5,852,233 A | 12/1998 | Arnold et al. | |
| 5,857,974 A | 1/1999 | Eberle et al. | |
| 5,865,178 A | 2/1999 | Yock | |
| 5,872,879 A | 2/1999 | Hamm | |
| 5,876,344 A | 3/1999 | Baker et al. | |
| 5,894,531 A | 4/1999 | Alcoz | |
| 5,921,931 A | 7/1999 | O'Donnell et al. | |
| 5,938,609 A | 8/1999 | Pomeranz | |
| 5,938,615 A | 8/1999 | Eberle et al. | |
| 5,944,687 A * | 8/1999 | Benett et al. | 604/22 |
| 5,980,117 A | 11/1999 | Feuer et al. | |
| 6,039,701 A | 3/2000 | Sliwa et al. | |
| 6,049,958 A | 4/2000 | Eberle et al. | |
| 6,057,927 A | 5/2000 | Levesque et al. | |
| 6,078,831 A | 6/2000 | Belef et al. | |
| 6,080,109 A | 6/2000 | Baker et al. | |
| 6,100,969 A | 8/2000 | Perez | |
| 6,111,645 A | 8/2000 | Tearney et al. | |
| 6,123,673 A | 9/2000 | Eberle et al. | |
| 6,134,003 A | 10/2000 | Tearney et al. | |
| 6,210,339 B1 | 4/2001 | Kiepen et al. | |
| 6,222,970 B1 | 4/2001 | Wach et al. | |
| 6,228,078 B1 | 5/2001 | Eggers et al. | |
| 6,238,347 B1 | 5/2001 | Nix et al. | |
| 6,248,076 B1 | 6/2001 | White et al. | |
| 6,261,246 B1 | 7/2001 | Pantages et al. | |
| 6,282,011 B1 | 8/2001 | Tearney et al. | |
| 6,283,920 B1 | 9/2001 | Eberle et al. | |
| 6,292,610 B1 * | 9/2001 | O'Rourke et al. | 385/52 |
| 6,306,096 B1 | 10/2001 | Seward et al. | |
| 6,315,732 B1 | 11/2001 | Suorsa et al. | |
| 6,379,325 B1 | 4/2002 | Benett et al. | |
| 6,421,164 B2 | 7/2002 | Tearney et al. | |
| 6,494,836 B2 | 12/2002 | Ogawa | |
| 6,575,965 B1 | 6/2003 | Fitch et al. | |
| 6,585,660 B2 | 7/2003 | Dorando et al. | |
| 6,618,916 B1 | 9/2003 | Eberle et al. | |
| 6,659,957 B1 | 12/2003 | Vardi et al. | |
| 6,779,257 B2 | 8/2004 | Kiepen et al. | |
| 6,783,494 B2 | 8/2004 | Ogawa | |
| 6,907,163 B2 | 6/2005 | Lewis | |
| 6,948,859 B2 * | 9/2005 | Anderson | 385/88 |
| 7,082,238 B2 * | 7/2006 | Nishimura | 385/48 |
| 7,184,148 B2 | 2/2007 | Alphonse | |
| 7,190,464 B2 | 3/2007 | Alphonse | |
| 7,242,480 B2 | 7/2007 | Alphonse | |
| 7,242,832 B2 | 7/2007 | Carlin et al. | |
| 7,245,789 B2 | 7/2007 | Bates et al. | |
| 7,417,740 B2 | 8/2008 | Alphonse et al. | |
| 7,447,388 B2 | 11/2008 | Bates et al. | |
| 7,527,594 B2 | 5/2009 | Vardi et al. | |
| 7,599,588 B2 | 10/2009 | Eberle et al. | |
| 7,660,492 B2 | 2/2010 | Bates et al. | |
| 2001/0021843 A1 | 9/2001 | Bosselmann et al. | |
| 2002/0039463 A1 | 4/2002 | Degertekin et al. | |
| 2002/0041735 A1 | 4/2002 | Cai et al. | |
| 2003/0026546 A1 | 2/2003 | Deliwala | |
| 2003/0187369 A1 | 10/2003 | Lewis et al. | |
| 2004/0067000 A1 | 4/2004 | Bates et al. | |
| 2004/0116800 A1 * | 6/2004 | Helfer et al. | 600/411 |
| 2004/0182315 A1 * | 9/2004 | Laflamme et al. | 118/715 |
| 2005/0131289 A1 | 6/2005 | Aharoni et al. | |
| 2005/0238292 A1 * | 10/2005 | Barnes et al. | 385/78 |
| 2006/0067616 A1 | 3/2006 | Kanji et al. | |
| 2007/0116408 A1 | 5/2007 | Eberle et al. | |
| 2007/0133925 A1 | 6/2007 | Bates et al. | |
| 2008/0077225 A1 | 3/2008 | Carlin et al. | |
| 2008/0119739 A1 | 5/2008 | Vardi et al. | |
| 2009/0059727 A1 | 3/2009 | Bates et al. | |

FOREIGN PATENT DOCUMENTS

| | | |
|---|---|---|
| DE | 2363984 A1 | 6/1975 |
| EP | 0 478 410 A1 | 4/1992 |
| EP | 0478410 A1 | 4/1992 |
| EP | 1152240 A2 | 11/2001 |
| GB | 2 270 159 A | 3/1994 |
| GB | 2270159 A | 3/1994 |
| JP | 05015536 A2 | 1/1993 |
| JP | 05220152 | 8/1993 |
| WO | WO 99/58059 | 11/1999 |
| WO | WO-9958059 A1 | 11/1999 |
| WO | WO-0049938 A1 | 8/2000 |
| WO | WO-01/21244 | 3/2001 |
| WO | WO-0219898 A3 | 3/2002 |
| WO | WO 02/054948 | 7/2002 |
| WO | WO-02054948 A1 | 7/2002 |
| WO | WO-02075404 A1 | 9/2002 |
| WO | WO-03057061 | 7/2003 |
| WO | WO-2004008070 | 1/2004 |
| WO | WO-2004029667 | 4/2004 |
| WO | WO-2004032746 A2 | 4/2004 |
| WO | WO-2004077100 | 9/2004 |
| WO | WO-2004090484 | 10/2004 |
| WO | WO-2007062050 A2 | 5/2007 |
| WO | WO-2007062050 A3 | 5/2007 |

OTHER PUBLICATIONS

"U.S. Appl. No. 09/623,248, Notice of Allowance mailed Jul. 11, 2003", 8 pgs.

"U.S. Appl. No. 09/623,248, Request for Continued Examination filed Apr. 14, 2003", 6 pgs.
"U.S. Appl. No. 09/623,248, Supplemental Notice of Allowability mailed Oct. 7, 2003", 6 pgs.
"U.S. Appl. No. 09/623,248, Notice of Allowance mailed Jan. 13, 2003", 7 pgs.
"U.S. Appl. No. 09/623,248 Notice of Allowance mailed Jan. 13, 2003", 8 pgs.
"U.S. Appl. No. 09/623,248 Notice of Allowance mailed Jun. 2, 2003", 10 pgs.
"U.S. Appl. No. 09/623,248 Notice of Allowance mailed Jul. 11, 2003", 8 pgs.
"U.S. Appl. No. 10/266,082, Amendment and Response filed Jul. 5, 2006 to Office Action mailed Apr. 5, 2006", 9 pgs.
"U.S. Appl. No. 10/266,082, Amendment and Response filed Jan. 3, 2006 to Office Action mailed Oct. 4, 2005", 10 pgs.
"U.S. Appl. No. 10/266,082, Final Office Action mailed Oct. 4, 2005", 7 pgs.
"U.S. Appl. No. 10/266,082, Notice of Allowance Aug. 26, 2004", 8 pgs.
"U.S. Appl. No. 10/266,082, Notice of Allowance mailed Jan. 12, 2005", 5 pgs.
"U.S. Appl. No. 10/266,082, Notice of Allowance mailed Jan. 16, 2007", 5 pgs.
"U.S. Appl. No. 10/266,082, Notice of Allowance mailed Mar. 22, 2007", 5 pgs.
"U.S. Appl. No. 10/266,082, Notice of Allowance mailed Sep. 22, 2006", 4 pgs.
"U.S. Appl. No. 10/266,082, Office Action mailed Apr. 5, 2006".
"U.S. Appl. No. 10/685,226, Response filed Apr. 18, 2007 to Non-Final Office Action mailed Jan. 18, 2007", 10 pgs.
"U.S. Appl. No. 10/685,226 Advisory Action mailed Apr. 17, 2006", 4 pgs.
"U.S. Appl. No. 10/685,226 Final Office Action mailed Jan. 13, 2006", 7 pgs.
"U.S. Appl. No. 10/685,226 Non Final Office Action mailed Jan. 18, 2007", 6 pgs.
"U.S. Appl. No. 10/685,226 Non Final Office Action mailed Jun. 15, 2005", 12 pgs.
"U.S. Appl. No. 10/685,226 Non Final Office Action mailed Jul. 24, 2006", 9 pgs.
"U.S. Appl. No. 10/685,226 Response filed Mar. 13, 2006 to Final Office Action mailed", 12 pgs.
"U.S. Appl. No. 10/685,226 Response filed Oct. 14, 2005 to Non Final Office Action mailed Jun. 15, 2005", 15 pgs.
"U.S. Appl. No. 10/685,226, Notice of Allowance mailed Oct. 18, 2007", 5 pgs.
"U.S. Appl. No. 11/285,449 Notice of Allowance mailed on May 27, 2009", 8 pgs.
"U.S. Appl. No. 11/285,499, Amendment and Response filed May 27, 2008 to Final Office Action mailed Jan. 25, 2008", 9 pages.
"U.S. Appl. No. 11/285,499, Non-Final Office Action mailed May 16, 2007", 24 pgs.
"U.S. Appl. No. 11/285,499 Non Final Office Action mailed May 16, 2007", 24 pgs.
"U.S. Appl. No. 11/285,499, Response filed Oct. 16, 2007 to Non-Final Office Action mailed May 16, 2007", 11 pgs.
"U.S. Appl. No. 11/285,499 Non-Final Office Action mailed on Nov. 13, 2008", 10 pgs.
"U.S. Appl. No. 11/285,499, Response filed Apr. 13, 2009 to Non Final Office Action mailed Nov. 13, 2008", 14 pgs.
"U.S. Appl. No. 11/674,568, Restriction Requirement mailed Sep. 17, 2007", 6 pgs.
"U.S. Appl. No. 11/674,568, Restriction Requirement mailed Sep. 17, 2007", 6 pgs.
"U.S. Appl. No. 11/674,568, Notice of Allowance Mailed Jun. 25, 2008", 5.
"U.S. Appl. No. 12/263,978, Notice of Allowance mailed Sep. 22, 2009", 15 Pgs.
"U.S. Appl. No. 11/674,568, Response filed Apr. 21, 2008", (7).
"U.S. Appl. No. 11/285,499, Final Office Action mailed Jan. 25, 2008", 11 pgs.
"U.S. Appl. No. 11/674,568 Non-Final Office Action Mailed Jan. 7, 2008", 15.
"Canadian Patent Application No. 2,348,580, Office Action mailed Feb. 20, 2007", 2 pgs.
"Canadian Patent Application No. 2,348,580, Response filed Aug. 16, 2007 to Office Action mailed Feb. 20, 2007", 7 pgs.
"European Application No. 99950325.3, Communication dated Jul. 28, 2004", 5 pgs.
"European Application No. 99950325.3, Response filed Feb. 7, 2005 to Official Action mailed Jul. 28, 2004", 11 pgs.
"European Search Report for corresponding European Application No. EP 05 02 4287", (Dec. 16, 2005), 3 pgs.
"International Preliminary Examination Report (IPER)", PCT/US03/31280, (Feb. 1, 2005).
"International Search Report and Written Opinion for Application No. PCT/US2006/045080", 16 Pages.
"Optical Review", vol. 4 .No. 6, (Nov. / Dec. 1997).
"Partial International Search Report for corresponding PCT Application No. PCT/US2006/045080", (Mar. 9, 2007), 3 pgs.
"PCT Application No. PCT/US2003/031280 International Search Report mailed Jul. 19, 2004", 8 pgs.
"PCT Application No. PCT/US2003/031280 Written Opinion mailed Jan. 14, 2005", 16 pgs.
"PCT Application No. PCT/US2003/031280, Amendment and Response filed Jan. 19, 2005 to Written Opinion mailed Jan. 14, 2005", 15 pgs.
"PCT Application No. PCT/US2006/045080 mailed May 16, 2007", 16 pgs.
"PCT Application No. PCT/US2006/045080, International Search Report mailed May 16, 2007", 6 pgs.
"PCT Notification of Transmittal of the International Search Report or the Declaration", *European Patent Office*, PCT/US03/31280, (Jul. 19, 2004), 9 pages.
"PCT Written Opinion", PCT/US03/31280, (Jan. 14, 2005), 7 pages.
"Published International Search Report for PCT/US2003/031280 (WO 2004/032746 A3)", (Apr. 22, 2004), 7 pages.
"Tissue Characterization through Ultrasonic Backscatter", http://www.brl.uiuc.edu/Projects/backscatter.htm, (viewed web site on Sep. 25, 2002), pp. 1-5.
06838195.3, "European Application Serial No. 06838195.3 , Office action Mailed Jul. 27, 2009", 4 pgs.
2000-547913, "Application No. 2000-547913, Office Action Mailed Feb. 13, 2009", 3 pgs.
2000-547913, "Japan application serial No. 2000-547913 , office action mailed on Jun. 23, 2009", 3.
Bates, K. N., "A High Acuity 3D Acoustic Imaging System", *Proceedings., 1995 IEEE Ultrasonics Symposium*, 2, (Nov. 7-10, 1995), 1245-1250.
Bates, K. N., "A One Dimensional Phased Array Imaging System", *Ph.D. Dissertation, Applied Physics, Standford University*, (1982).
Bates, K. N., et al., "PEOATS and ESOATS", *IEEE Ultrasonics Symposium Proceedings*, 1979 (Sep. 26-28, 1979), 189-194.
Bates, K. N., "Tolerance Analysis for Phased Arrays", *Acoustic Imaging*, 9, (1980), 239-262.
Bates, Kenneth N, "A high acuity 3-D acoustic imaging system", *Proceedings., 1995 IEEE Ultrasonics Symposium*, 2, (Nov. 7-10, 1995), 1245-1250.
Bates, Kenneth N., et al., "Digitally Controlled Electronically Scanned and Focused Ultrasonic Imaging System", *IEEE Ultrasonics Symposium Proceedings*, 1979, (Sep. 26-28, 1979), 216-220.
Blotekjaer, K., "Theoretical concepts of a novel Vernier-based fringe-counting fibre optic sensor", *IEE Proceedings, Optoelectronics*, 144(3), (Jun. 1997), 126-129.
Brady, G. P, et al., "Simultaneous measurement of strain and temperature using the first- and second-order diffraction wavelengths of Bragg gratings", *IEE Proceedings, Optoelectronics*, 144(3) (Jun. 1997), 156-161.
Buma, T., et al., "A high frequency ultrasound array element using thermoelastic expansion in PDMS", *Proceedings of the 2001 IEEE Ultrasonics Symposium*, 2, (Oct. 7-10, 2001), 1143-1146.

Buma, T., et al., "A high frequency ultrasound array element using thermoelastic expansion in PDMS", *2001 IEEE Ultrasonics Symposium. Proceedings. An International Symposium*, 2(2), (Oct. 7-10, 2001), 1143-6.

Buma, T., et al., "A high-frequency, 2-D array element using thermoelastic expansion in PDMS", *IEEE Transactions on Ultrasonics, Ferroelectrics and Frequency Control*, 50(9), (Sep. 2003), 1161-1176.

Buma, T., et al., "High Frequency Ultrasonic Imaging Using Optoacoustic Arrays", *Proceedings of the Proceeding of the 2002 IEEE Ultrasonics Symposium*, 1, Invited paper, (Oct. 8-11, 2002), 571-580.

Buma, T., et al., "High Frequency Ultrasound Array Element using Thermoelastic Expansion in an Elastomeric Film", *Applied Physics Letters*, 79(4), (Jul. 23, 2001), 548-550.

Buma, T., et al., "High-frequency ultrasound imaging using optoacoustic arrays", *Proceedings of the SPIE—The International Society for Optical Engineering*, 4687, (2002), 99-109.

Buma, T., et al., "Thermoelastic Expansion versus Piezoelectricity for High Frequency 2-D Arrays", *IEEE Transactions on Ultrasonics, Ferroelectrics and Frequency Control*, 50(8), (Aug. 2003), 1065-1068.

Buma, T., et al., "Thermoelastic Generation of Continuous Lamb Waves for Microfluidic Devices", *Proceeding of the 2003 IEEE Ultrasonics Symposium*, (2003), 150-153.

Buma, T., et al., "Thermoelastic Generation of Ultrasound Using anErbium Doped Fiber Amplifier", *Proceeding of the 1999 IEEE Ultrasonics Symposium*, 2, (Oct. 17-20, 1999), 1253-1256.

Davis, M. A, et al., "Simultaneous measurement of temperature and strain using fibre Bragg gratings and Brillouin scattering", *IEE Proceedings, Optoelectronics*, 144(3), (Jun. 1997), 151-155.

Feced, R., et al., "Advances in high resolution distributed temperature sensing using the time-correlated single photon counting technique", *IEE Proceedings, Optoelectronics*, 144(3), (Jun. 1997), 183-188.

Furstenau, N., et al., "Extrinsic Fabry-Perot interferometer vibration and acoustic sensor systems for airport ground traffic monitoring", *IEE Proceedings, Optoelectronics*, 144(3), (Jun. 1997), 134-144.

Hamilton, J. D., et al., "An active optical detector for high frequency ultrasound imaging", *Proceedings of the 1997 IEEE Ultrasonics Symposium*, 1, (Oct. 5-8, 1997), 753-756.

Hamilton, J. D., et al., "High frequency optoacoustic arrays using etalon detection", *IEEE Transactions on Ultrasonics, Ferroelectrics and Frequency Control*, 47(1), (Jan. 2000), 160-169.

Hamilton, J. D., et al., "High Frequency Ultrasound Imaging Using an Active optical Detector", *IEEE Transactions on Ultrasonics, Ferroelectrics and Frequency Control UFFC-45*, 719-727.

Hamilton, J. D., et al., "High Frequency Ultrasound Imaging with Optical Arrays", *IEEE Transactions on Ultrasonics, Ferroelectrics and Frequency Control*, 45(1), (Jan. 1998), 216-235.

Hamilton, J. D., et al., "Optical Arrays for High Frequency Ultrasound Imaging", *Proceedings of the 1996 IEEE Ultrasonics Symposium*, (1996), 1419-1422.

Karl, W Clem, "Multi-Sensor Fusion for Atherosclerotic Plaque Characterization", *Boston Univ—MDSP*, 15 pages, (obtained from the internet on Sep. 25, 2002, http://www.censsis.neu/Education/StudentResearch/2001/posters/weisensell)r!.pdf.

Komiyama, N., et al., "Tissue Characterization of Atherosclerotic Plaques by Intravascular Ultrasound Radiofrequency Signal Analysis: An In Vitro Study of Human Coronary Arteries", *Entrez-PubMed*—(http://www.ncbi.nlm.nih.gov/entrez/query)—viewed web site on Sep. 25, 2002, pp. 1-2.

Krass, S., et al., "P3.4 Pattern Reconition Algorithms for Tissue Characterisation in Intracoronary Ultrasound Imaging: Test Data Set and Results of Computerised Texture Analysis", *2nd Medical Clinic, Univ-Mainz, Germany*—(http://www.uni-mainz.de/Cardio/incis/Data/p3_4.htm)—view wen site on Sep. 25, 2002, pp. 1-3.

Lockey, R. A, et al., "Multicomponent time-division-multiplexed optical fibre laser Doppler anemometry", *IEE Proceedings, Optoelectronics*, 144(3), (Jun. 1997), 168-175.

Macpherson, W. N, et al., "Phase demodulation in optical fibre Fabry-Perot sensors with inexact phase steps", *IEE Proceedings, Optoelectronics*, 144(3), (Jun. 1997), 130-133.

McCulloch, S., et al., "Development of a fibre optic micro-optrode for intracellular pH measurements", *IEE Proceedings, Optoelectronics*, 144(3), (Jun. 1997), 162-167.

Mintz, Gary S., et al., "American College of Cardiology Clenical Expert Consensus Document on Standards for Acquisition, Measurement and Reporting of Intravascular Ultrasound Studies (IVUS)", *Journal of the American College of Cardiology*, 37(5), (Apr. 2001), 1478-1492.

O'Donnell, M., "New Imaging Technologies for Ultrasonography", *J Med Ultrason.*, 27(4), Presented at the 73rd Japan Society of Ultrasound in Medicine Meeting, Invited Paper, (2000), 356-357.

O'Donnell, M., et al., "Optoacoustics: high frequency ultrasonic array imaging", *Proceedings of 17th International Congress on Acoustics*, vol. IV, Biomedicine, Acoustics in Medicine, Invited Presentation at the 17th Intl Congress on Acoustics, Rome, (Sep. 2-7, 2001), 2-3.

Othonos, A., et al., "In Section 7.9 Bragg Gating Fiber Laser Sensors from Fiber Bragg Gratings: fundamentals and applications in telecommunications and sensing", *(1999 Artech House, Inc.)*, 355-367.

Pepine, Carl J., et al., "Improving Diagnostic and Therapeutic Outcomes Through Advanced Intravascular Imaging", *Vascular Technologies, Inc.*, (1989).

Scully, P. J., "UV Laser Photo-induced Refractive Index Changes in Poly-Methyl-Meth-Acrylate and Plastic Optical Fibres for Application as Sensors and Devices", *Central Laser Facility Annual Report*, 1999/2000, 145-147.

Spisar, M., et al., "Stabilized, Resonant Optoacoustic Array Detectors for Medical Imaging", *Proceedings of the World Congress on Ultrasonics*, Paris, France, (Sep. 7-10, 2003), 25-28.

Stefanadis, Christodoulos, et al., "Identification and Stabilization of Vulnerable Atherosclerotic Plaques: The Role of Coronary Thermagraphy and External Heat Delivery", *Identification and Stabilization of Vulnerable Atherosclerotic Plagues IHJ*—(viewed web site on Sep. 25, 2002), http://www.indianheartjournal.org, (2001), 1-10.

Surowiec, J., et al., "A Novel Miniature Optical Fibre Probe for MHz Frequency Ultrasound", *Proceedings, IEEE Ultrasonics Symposium*, vol. 2, (Nov. 3-6, 1996, San Antonio, TX), (1996), 1051-1054.

Takahashi, N., et al., "Underwater Acoustic Sensor using Fiber Bragg Grating", *The Optical Society of Japan*, 4(6), (Nov. 1997), 691-694.

Tanaka, S., et al., "Fibre optic spectral polarimetry for sensing multiple stress-loaded locations along a length of fibre", *IEE Proceedings, Optoelectronics*, 144(3), (Jun. 1997), 176-182.

Wahle, Andreas, et al., "Accurate Visualization and Quantification of Coronary Vasculature by 3-D/4-D Fusion from Biplane Angiography and Intravascular Ultrasound", *In: Biomonitoring and Endoscopy Technologies*; I. Gannot et al., eds, (Jul. 5-6, 2000), 144-155.

Yoshino, T., et al., "Spiral fibre microbend sensors", *IEE Proceedings, Optoelectronics*, 144(3), (Jun. 1997), 145-150.

* cited by examiner

OPTICAL IMAGING PROBE CONNECTOR

RELATED APPLICATION

This patent application is a continuation application of U.S. patent application Ser. No. 11/285,499, which was filed on Nov. 22, 2005, now U.S. Pat. No. 7,599,588 and which is incorporated herein by reference in its entirety.

TECHNICAL FIELD

This patent document pertains generally to imaging, and more particularly, but not by way of limitation, to an optical imaging probe connector.

BACKGROUND

Bates et al. United States Published Patent Application US 2004/0067000 discusses a minimally-invasive optical-acoustic device for vascular and non-vascular imaging. It discloses an elongated optical imaging guidewire, catheter, or like probe with one or more ultrasound transducers at its distal end to provide ultrasound energy to nearby tissue or the like. Light energy produced at the external instrumentation is transmitted to the distal end of the implanted instrument, where it is converted to sound energy that is directed at nearby tissue or the like. Sound energy returned by such tissue modulates light energy at the distal end of the implanted section of the instrument. Such modulated light is then communicated to back to the proximal end of the instrument, and then to externally located diagnostic instrumentation.

SUMMARY

The present Applicant has recognized that the imaging system can use different sections of optical fiber, e.g., one section for inserting into a patient, and the other section for connecting to the external instrumentation. Efficient communication of information between external instrumentation and the ultrasound transmitting or receiving element relies on efficient light coupling between optical fibers included in the catheter.

However, optical fibers are difficult to reliably align accurately and quickly because, for the present application, the typical single-mode optical fiber transmission core is less than 10 micrometers in diameter (e.g., 3-4 micrometers in core diameter; 15-30 micrometers in outer diameter). A small misalignment between fiber cores may produce significant coupling losses—particularly because optical fiber also tends to have a small numerical aperture. Moreover, efficient coupling of light between ends of multiple (e.g., 32) pairs of parallel optical fibers along the instrument may be difficult using fiber cut from different cable regions or different cable. The relative spatial variations of the optical fibers running along the cable length make it unlikely that all fiber ends can be mechanically aligned if later joined.

In the context of a medical imaging instrument, ease of alignment in coupling a minimally-invasive instrument to an external instrumentation system is an important consideration. In a medical procedure, such instrumentation coupling time may affect the length of time a patient is exposed to risk, such as from bacteria or anesthesia. Moreover, product costs are influenced by the complexity of a design and how easily it can be manufactured. Reducing the number of components needed for manufacturing and assembling an optical fiber coupler will likely yield a less expensive final product, which will help reduce health care costs. For these and other reasons, the present applicant has recognized that there is an unmet need in the art for improved connectors for optical imaging catheters.

In one embodiment, this document discloses an optical coupler. The optical coupler includes a housing and at least one first optical fiber having a beveled end located at the housing. The coupler is configured to accept an elongated "probe" member, its distal end configured for imaging within an organism. The elongated probe member includes at least one second optical fiber having a beveled end that butts against and mates in self-alignment to the beveled end of the first optical fiber to couple light between the beveled end of the first optical fiber and the beveled end of the second optical fiber.

Moreover, in certain examples, an external instrumentation lead portion (e.g., attached to the coupler) and the probe portion are manufactured from the same optical cable assembly, such as by cutting the same optical cable assembly into the separate external instrumentation lead portion and the probe portion. The benefit of dividing the optical cable assembly into probe and external instrumentation lead portions after the optical cable assembly is manufactured from a center body and peripheral optical fibers, is that the optical fibers will be substantially perfectly aligned at the division location. Therefore, each connector will uniquely fit each imaging probe optimally, which is okay because both are typically discarded after a single patient use.

This summary is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

1. Example of a Self-Aligning Optical Imaging Catheter

Figure 1A:
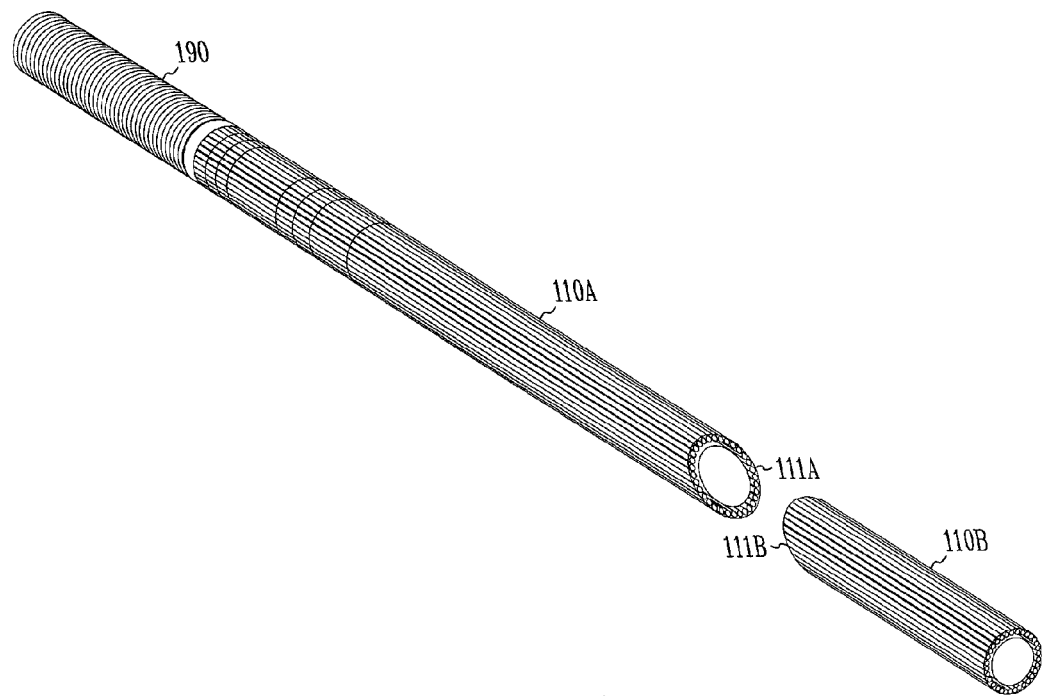
FIG. 1A is a isometric view illustrating generally one example of an optical imaging device after separation into a probe portion and an external instrumentation lead portion.
Figure 1B:
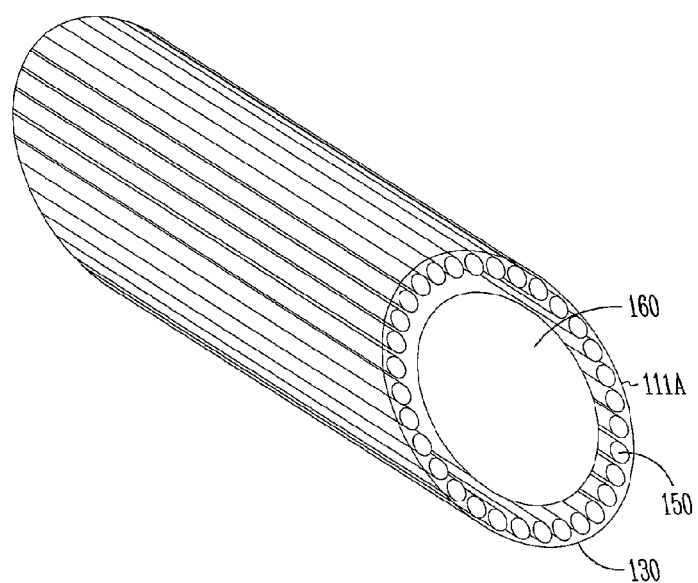
FIG. 1B is an expanded isometric view illustrating generally one example of the probe portion.

FIGS. 1A-1B illustrate an isometric view of an example of an optical imaging probe. In this example, optical fibers 150 are distributed around the outer circumference of an elongate center body 160. When this assembly of the (e.g., 32) optical fibers 150 around the body 160 is manufactured, the optical fibers 150 are typically encapsulated along the length of the assembly in a protective coating, such as a plastic matrix. The placement of the optical fibers 150 around the center body 160 may have a periodic or other variation, such as due to equipment or process variations. Although it may be possible to seat each of the optical fibers 150 accurately upon the center body 160, there is also typically an additional variation in core-to-cladding concentricity of the optical fibers 150, which can amount to 1 micrometer or more.

In the example of FIG. 1A, the assembly is manufactured with an extra length. Whereas about 195 cm would generally be enough length for the minimally invasive probe portion, in this example, an extra amount (e.g., 200 cm more) is provided. Then, the assembly of the optical fibers 150 and the body 160 is physically angularly cut or otherwise separated into two mated sections: a (e.g., 195 cm) probe portion 110A, and an (e.g., 200 cm) external instrumentation lead portion 110B. Moreover, by cutting at such a beveled angle, these two portions can advantageously then be butt-coupled against each other in self-alignment using a coupler housing to which one of these portions is affixed, and to which the other of these portions can be secured. Furthermore, by appropriate beveling, back reflection of light radiation can be reduced or minimized. In general, the amount of beveling for obtaining tactile self-alignment will exceed the amount of beveling needed for avoiding back reflection of light without obtaining self-alignment. For example, for avoiding back reflection of light without obtaining self-alignment, a bevel angle of about 8 degrees from a perpendicular cut is typically used. For tactile self-alignment, a bevel angle of between about 20 degrees and about 60 degrees from such a perpendicular cut is used, which also avoids back reflection as well as obtaining the desired tactile self-alignment. In another example, a bevel angle of between about 30 degrees and about 50 degrees from such a perpendicular cut is used, which also avoids back reflection as well as obtaining the desired tactile self-alignment. In yet a further example, a bevel angle of about 45 degrees from such a perpendicular cut is used, which also avoids back reflection as well as obtaining the desired tactile self-alignment.

The optical fibers 150 may be included with the body 160 at the time the body 160 is manufactured, or such optical fibers 150 may be later secured to the body 160. The assembly of the optical fibers 150 and the body 160 may contain fewer or more optical fibers 150 than shown in FIGS. 1A-1B. In certain examples, the optical fibers 150 are embedded in a relatively soft plastic coating material. However, cutting the assembly of the body 160 and the optical fibers 150 (e.g., with a diamond saw) may fray the ends of the probe portion 110A or the external instrumentation lead portion 110B, or both. Such fraying increases the difficulty of obtaining proper alignment between the probe portion 110A or the external instrumentation lead portion 110B. Several techniques can be employed to protect or preserve the position of the optical fibers 150 during the cutting process. In one such example, in which the optical fibers 150 are secured to the body 160 by a relatively soft plastic matrix, the relatively soft plastic matrix is selectively hardened or replaced with relatively hard plastic or epoxy in the area which is to be cut to form the connector. In another example, an outside layer of the plastic matrix is replaced by a thin-walled hard tube (e.g., metallic or polyimide). This will encase the optical fibers 150 to prevent excessive movement of the plastic matrix and fraying of the ends. After separation, both the probe portion 110A and the external instrumentation lead portion 110B will have a portion of the tube remaining. The remaining tube would also protect a proximal portion of the probe portion 110A during use, such as from threading an angioplasty balloon or a stent onto the probe portion 110A.

In certain examples, the process of cutting the assembly into mated portions 110A-B creates substantially mirrored or otherwise mating beveled probe proximal end 111A and external instrumentation lead proximal end 110B, respectively, at the location of separation. The probe 110A may be invasively introduced into body tissue, such as into vasculature or into a body orifice. The probe 110A may contain one of more transducer elements or sensors near its distal end 190. The external instrumentation lead portion 110B is typically connected at its distal end to diagnostic instrumentation located external to the patient's body. Light to and from the distal end 190 of the probe 110A is coupled between the probe portion 110A and lead portion 100B at their respective beveled proximal ends 111A and 111B.

In the example illustrated in FIGS. 1A and 1B, the optical fibers 150 are arranged about the body 160 in the longitudinal direction of the body 160. However, in an alternative example of the probe portion 110A or the instrumentation lead portion 110B, it may be preferable to spirally arrange the optical fibers 150 about the outer diameter of the body 160 along its length. This could be beneficial in distributing tensile stresses and compression forces more evenly between the fibers 150, for example, as the probe portion 110A of the device flexes and bends through the vasculature toward a target location. In general, a helical arrangement of optical fibers 150 may achieve greater flexibility or reliability. In this example, the fibers 150 may remain parallel to the longitudinal axis of the device in the region of the connector where the probe portion 110A and the instrumentation lead portion 110B are parted. Alternatively, if the spiral is maintained through such region of partition, it may be helpful to ensure that any lateral fiber displacement imparted by the spiral construction is substantially negligible for the given parting saw thickness so that the cores of the optical fibers 150 continue to substantially realign when the two separated ends are brought together. There may be a practical limit to the number of spiral wraps per linear length of the device in the region of the partition. Using a thinner parting saw blade will help ensure that such realignment occurs.

Figure 2A:
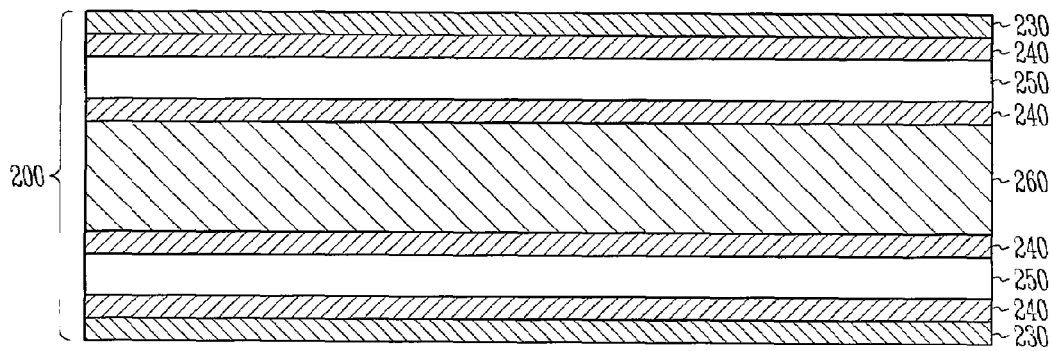
FIG. 2A is a cross-sectional side view illustrating generally one example of an optical cable assembly before beveled separation into a self-aligning probe portion and an external instrumentation lead portion.
Figure 2B:
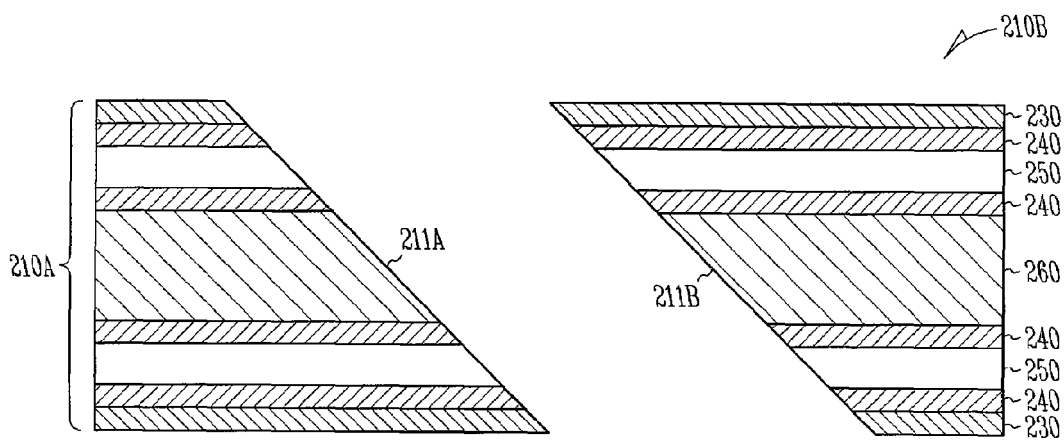
FIG. 2B is a cross-sectional side view illustrating generally one example of an optical cable assembly after separation into a probe portion and an external instrumentation lead portion.
Figure 2C:
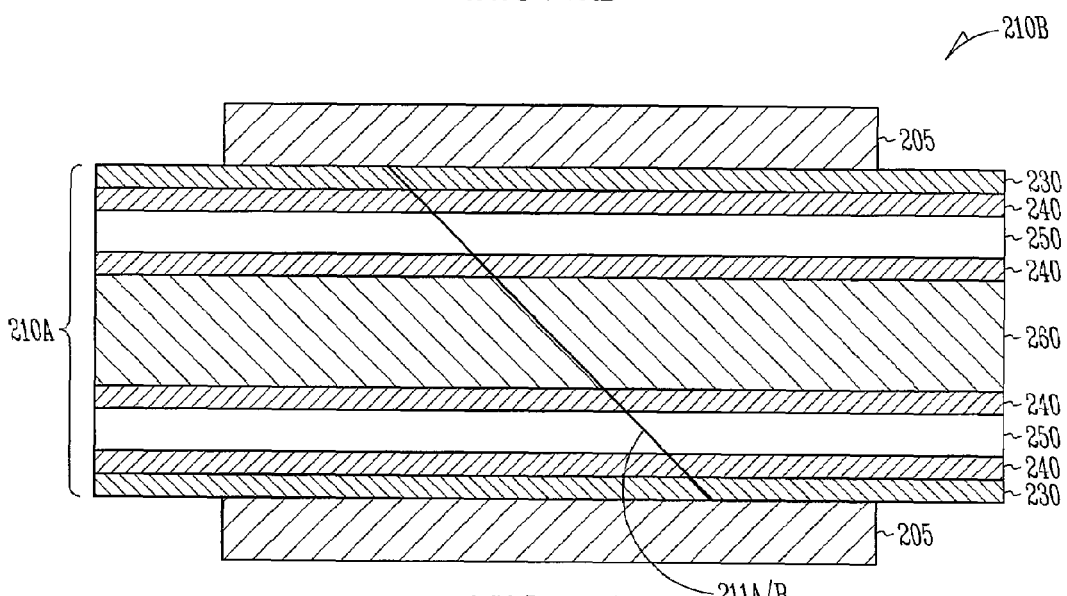
FIG. 2C is a cross-sectional side view illustrating generally one example of the separate probe and external instrumentation lead portions being butt-coupled in self-alignment.

FIGS. 2A-C are cross-sectional side views illustrating one example of how an optical cable assembly 200 is separated into two sections, so as to then provide substantially mating or mirrored beveled ends 211A and 211B, which provide the respective proximal ends 111A and 111B of FIG. 1A. In the example of FIGS. 2A-2C, only two optical fibers 150 of the optical cable assembly are illustrated, for ease in understanding and not by way of limitation.

FIG. 2A illustrates an example of the optical cable assembly 200 before separation into the probe portion 10A and the lead portion 110B. In this example, the then-unitary optical cable assembly 200 typically includes center body 260, optical fiber claddings 240, optical fibers 250, and a sheath 230 that encloses the optical fibers 250, center body 260 and claddings 240. Cladding 240 or sheath 230 may use the same or different material as center body 260. Center body 260, cladding 240, and sheath 230 may be formed at substantially the same time, or may be formed separately and later assembled to form the optical cable.

FIG. 2B illustrates an example of the optical cable after it has been angularly sawed into two sections, such as by using a thin dicing wheel or circular blade with a diamond edge blade, for example, or by using any other separation method, such as ultrasonic cutting, for example. After sawing, the probe portion 210A and the external instrumentation lead portion 210B will have substantially similar, mating or mirrored beveled surfaces. Variation in saw blade width may produce a small anti-parallel deviation at the beveled ends 211A and 211B. The beveled ends 211A and 211B may be further polished to reduce or remove surface damage or latent saw damage or subsurface defects, such as due to sawing, or to produce more parallel surfaces to further improve optical coupling, such as by reducing or minimizing scattering from the surfaces of such beveled ends 211A-B.

FIG. 2C illustrates the beveled end 211A of probe portion 210A in contact with the beveled end 211B of the external instrumentation lead portion 210B, and positioned within an ergonomically-shaped coupler housing 205 forming an optical coupler for coupling light between the probe portion 210A and the lead portion 210B. In certain examples, the external instrumentation lead portion 210B is permanently affixed to the coupler housing 205, such as by being inserted into the coupler housing 205 so as to obtain an interference fit, or by using an adhesive. The probe portion 210A is then inserted into the coupler housing 205 until it butt-couples in self-alignment against the external instrumentation lead portion 210B. Such convenient self-alignment promotes coupling of light between adjoining optical fibers 250 in respective probe and external instrumentation lead portions. The coupler housing 205 is typically formed of plastic, but in certain examples, may include an inner surface that is composed of precision fabricated straight wall metal, glass, or ceramic tubing.

In certain examples, an antireflective surface coating is used at the beveled ends 211A-B, or index matching fluid is used between the beveled ends 211A-B, such as for further improving the amount of light coupled between the ends of the optical fibers 250 of the probe portion 210A and the external instrumentation lead portion 210B. Index matching fluid typically has substantially the same refractive index as the optical fiber 250 at the desired wavelength of light used. It typically reduces or eliminates the likelihood of a fiber-air-fiber interface, which would likely cause undesirable reflections of light transmitted to and from the probe portion 210A or the external instrumentation portion 210B. A fiber-air-fiber interface may occur if the beveled ends 211A-B do not butt against each other in perfect mechanical contact when otherwise in optical alignment.

Figure 3:
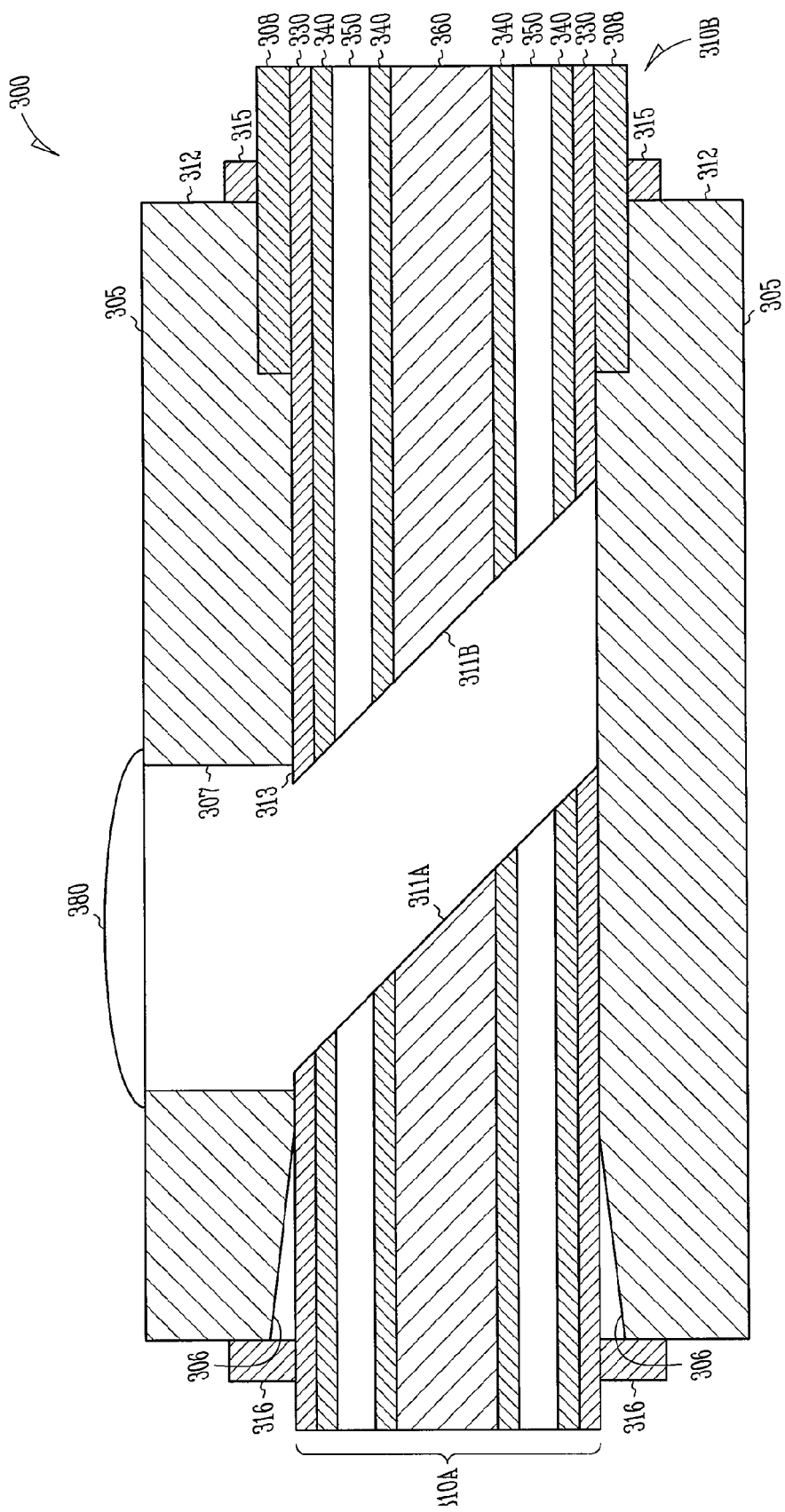
FIG. 3 is a cross-sectional schematic diagram illustrating generally one example of a self-aligning probe and external instrumentation lead portions using beveled ends.

FIG. 3 is a cross sectional side view schematic diagram illustrating one example of a connector 300 for aligning beveled ends of a probe portion 310A and an external instrumentation lead portion 310B. In one example, the beveled end 311B of the external instrumentation lead portion 310B is secured to protective sleeve 308, and may be further secured to a coupler housing 305 near the external instrumentation lead end of the housing 305 at 312, such as by using adhesive or other suitable material. In another example, the external instrumentation lead portion 310B may be secured to the housing 305, with or without being securing to the protective sleeve 308, such as by a compression clamp 315. The housing 305 may be metal, plastic, or other suitable material, and may be formed from more than one component.

In certain examples, the external instrumentation lead portion 310B is directly or indirectly secured to the housing 305 with the tip 313 of the beveled end 311B positioned within a perimeter of a view hole or port 307, such that it can be oriented toward a view lens 380, which is attached over the view hole 307, such as by using an adhesive or other suitable technique. The lens 380 may use one or more antireflective surface coatings to increase light transmission through the lens 380. The probe portion 310A is inserted into the housing 305; this is aided by a beveled housing surface 306, which forms a funnel-like structure to reduce or minimize any potential damage to the beveled end 311A of the probe portion 310A during such insertion into the housing 305. In certain examples, for aligning the beveled ends 311A-B, visible light (e.g., red light emitted from a diode, etc.) may be transmitted from the instrumentation lead portion 310B while the probe portion 310A is inserted into the housing 305. Such visible light exiting an optical fiber 350 at the beveled end 311B of the external instrumentation lead 310B is reflected by at least one optical fiber 350 at the beveled end 311A of the probe portion 310A through the view hole 307 toward the view lens 380. A user looking at the view lens 380 will observe maximum intensity of the reflected light when the probe portion 310A is properly oriented and aligned with respect to the external instrumentation lead portion 310B. In another example, light striking lens 380 is coupled to a photodetector, and the resulting signal from the photodetector similarly used for aligning the beveled ends 311A-B. In yet another example, lens 380 is omitted, and light propagating through view hole 307 is instead coupled directly to an external photodetector where the corresponding photodetector output signal is used for aligning the beveled ends 311A-B. In another example, the alignment light is coupled to an external photodetector by a lens 380 that is unsecured to the housing. The circumferential surface of the view hole 307 surface may be polished or coated with a reflective film to improve surface reflectivity of light used for aligning the beveled ends 311A-B.

During insertion of the probe portion 310A into the housing 305, the probe portion 310A may be rotated to obtain maximum alignment light reflected toward view lens 380 from the beveled end 311B of the external instrumentation lead portion 310B until the probe portion 310A and external instrumentation lead portion 310B butt in mechanical contact. More light is reflected toward the view hole 307 when the optical fibers 350 of the probe portion 310A and the external instrumentation lead portion 310B are best aligned. Then, when the beveled ends 311A-B of the probe portion 310A and the lead portion 310B are in mechanical contact with each other, maximum optical alignment is achieved and substantially all alignment light transmitted from external instrumentation lead portion 310B is coupled into the probe portion 310A, leaving no light for reflection towards the view hole 307. As discussed above, index matching fluid may be used between the beveled ends 311A-B to improve light coupling between the beveled ends 311A-B. The end of the probe portion 310A may be secured to the housing 305, such as by a compression clamp 316 secured to housing 305, or even by using an adhesive, if desired.

In the example of FIG. 3, such alignment of the probe portion 310A and the external instrumentation lead portion 310B using the view hole 307 is generally possible if the angle of the beveled end 311B is less than the critical angle for total internal reflection.

Figure 4:
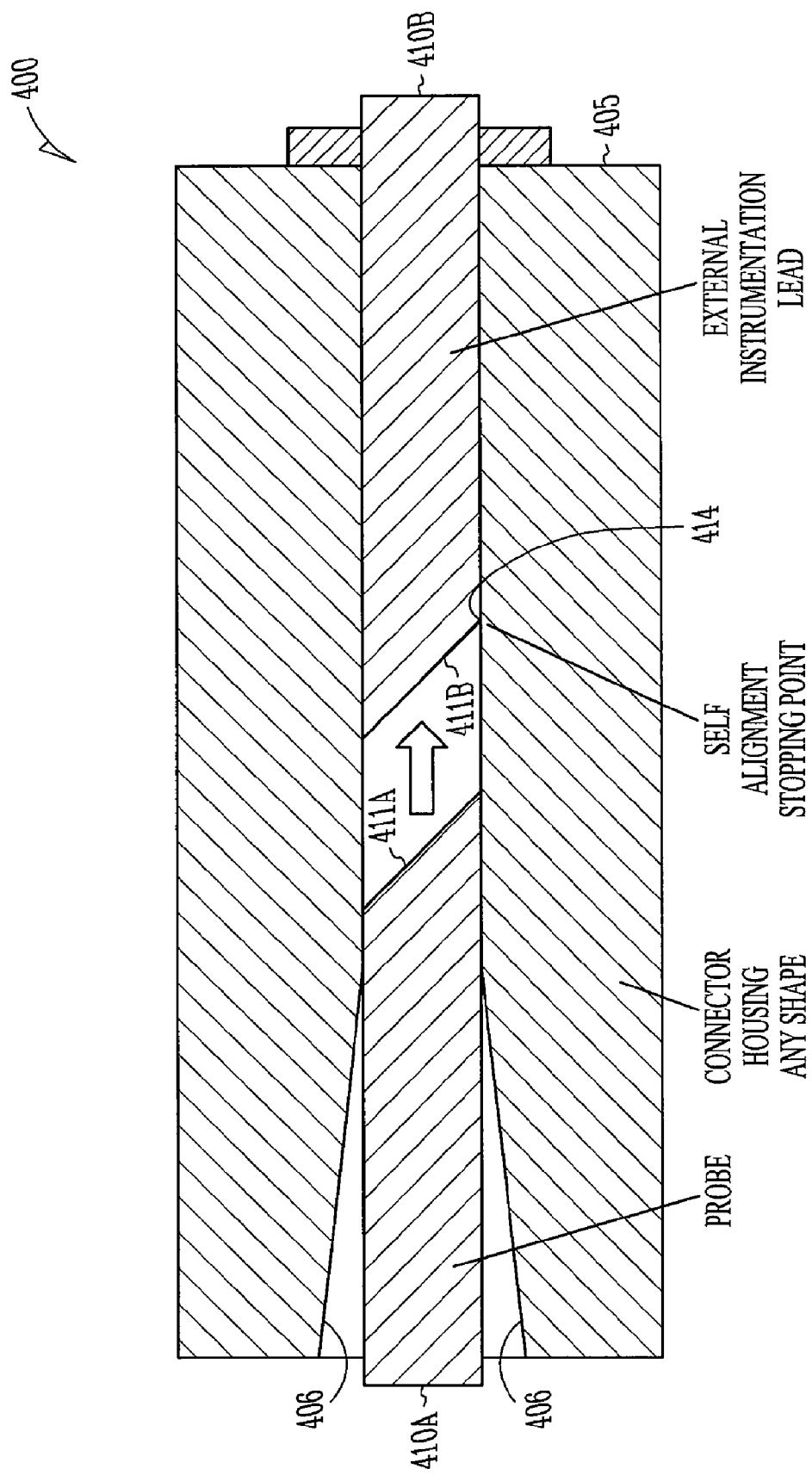
FIG. 4 is a cross-sectional schematic diagram illustrating generally one example of self-aligning beveled ends of probe and external instrumentation lead portions using a stop.

FIG. 4 is a cross-sectional side view schematic illustrating one example of a connector 400 for aligning beveled ends 411A and 411B of a respective probe portion 410A and an external instrumentation lead portion 410B at a stop 414. In certain examples, the external instrumentation lead portion 410B is secured to the coupler housing 405, such as with adhesive or other suitable technique near the beveled end 411B at stop 414 or at another suitable location. If necessary, a suitable solvent may be used to remove any stray adhesive from the optical surfaces of the beveled end 411B of the external instrumentation lead portion 410B. Then, the probe portion 410A is inserted into housing 405 until its beveled end 411A butts in mechanical contact with the beveled end 411B of the external instrumentation lead potion 410B. Because the external instrumentation lead portion 410B is secured at 414 to the inner surface of the housing 405, such as near the beveled end 411B, the beveled end 411A of the probe portion 410A is prevented from further traveling beyond the stop 414. In such an example, maximum optical alignment is achieved and substantially all light is coupled between the probe portion 410A and the external instrumentation lead portion 410B when their respective beveled ends 411A-B butt in mechanical contact at the stop 414. In certain examples, a beveled surface 406 of the housing 405 is provided to reduce the potential for damage to the beveled end 411A of the probe portion 410A during insertion. The probe portion 410A is secured to the housing 405, such as by a compression clamp 416 that is secured to the housing, or even by an adhesive or other suitable technique, if desired. The ends of the optical fibers 450 may use an antireflective surface coating or index matching fluid between their beveled ends to improve light coupling between the probe and external instrumentation lead portions 410A-B.

Figure 9:
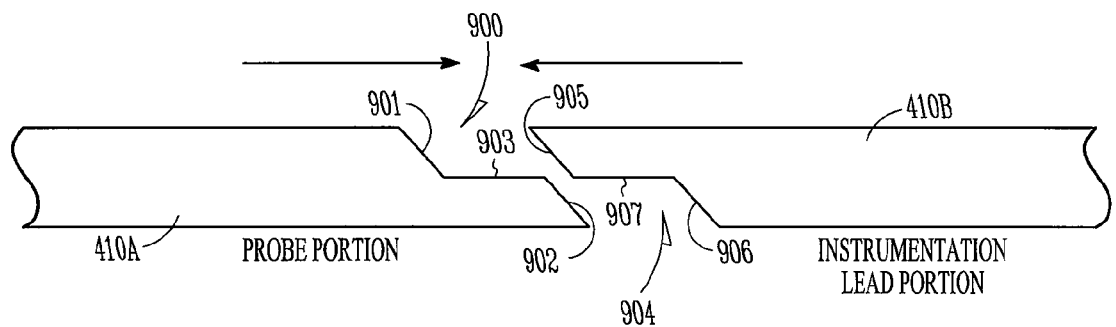
FIG. 9 is a side view illustrating generally one example of a keyed connection.

A number of beneficial features can be incorporated into any of the coupler housings described in this document, such as the coupler housings 205, 305, or 405. In one example, a soft fabric or other cleaning device is placed at the receptacle of the coupler housing that receives the probe portion to clean its end as it is received into the coupler housing. In another example, the coupler housing includes a flushing port (which may be the same or different from the viewing hole 307) for removing blood or other debris that may be accumulated during use, such as by flushing with saline or the like. In another example, the coupler housing includes an attachable syringe or other injection device for injecting index matching fluid (which could even include injecting medical grade silicone gel) into the connector cavity where the probe and external instrumentation lead portions come together. In yet another example, the coupler housing includes a gripping mechanism that attaches to the probe portion along its length without causing damage to its optical fibers. In another variation, the angular beveled ends of the probe portion and the external instrumentation lead portion is replaced by a longitudinal cut that creates semicircular or like mating sections that overlap between the probe portion and the external instrumentation lead. For example, FIG. 9 illustrates an example of a keyed connection in which the beveled end 900 of the probe portion 410A is separated into semicircular beveled portions 901 and 902, which are separated by a longitudinal edge 903. Similarly, the beveled end 904 of the instrumentation lead portion 410B is separated into semicircular beveled portions 905 and 906 separated by a longitudinal edge 907, such that the beveled end 904 mates to the beveled end 900. This example would provide a more discernable alignment that can be "felt" by the user. In another variation, the proximal end of the probe portion is conical (male/female) and self-aligning with a conical (female/male) end of the external instrumentation lead at the coupler housing.

Finally, the distal end of the external instrumentation lead (i.e., away from the coupler housing) will be interfaced to an opto-electronic imaging console. This can be achieved by using a commercially available multiple fiber connector, such as the MTP multi-fiber connector available from US Conec, Ltd. of Hickory, N.C. (see http://www.usconec.com/pages/product/connect/mtpcon/mainfrm.html). This connector can be customized to accept different diameter and numbers of optical fibers. The termination may be achieved by selectively removing the plastic matrix coating at the distal end of the external instrumentation lead. The individual fibers can be separated from the external instrumentation lead center body and individually placed in the holes in the connector. A hole may also be provided for the center body of the external instrumentation lead, such as to stabilize the connection.

2. Example of a Guide-Aligning Optical Imaging Device

Figure 5A:
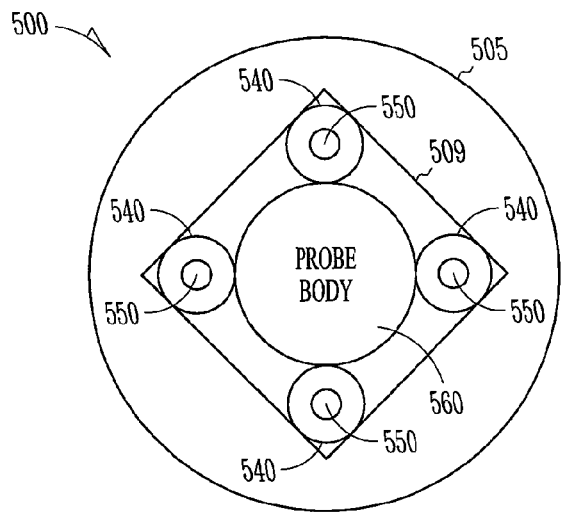
FIG. 5A is a cross-sectional end view illustrating generally one example of a connector using a guide.
Figure 5B:
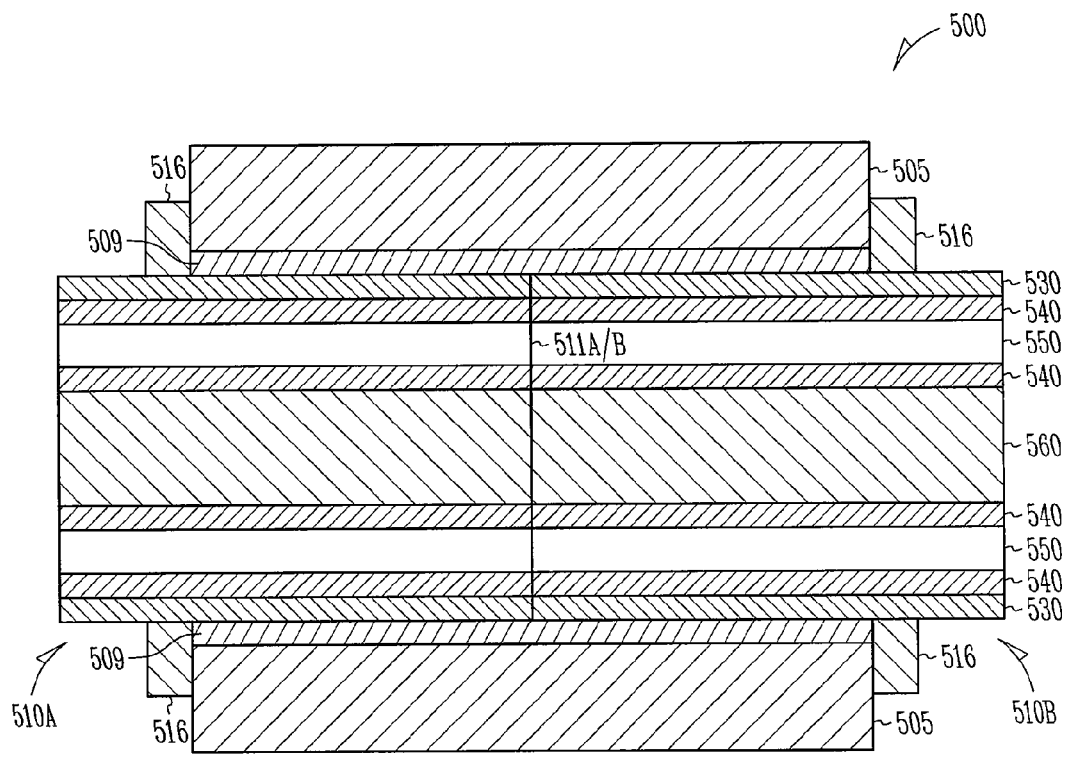
FIG. 5B is a cross-sectional side view illustrating generally one example of a connector using a guide.

FIGS. 5A and 5B are respective cross-sectional end and side views illustrating an example of an optical connector 500 for an optical imaging device using a guide 509 at an interior portion of a coupler housing 505. In this example, the guide 509 axially receives and accepts each of the probe portion 510A and the external instrumentation lead portion 510B in a particular orientation such that the optical fibers 550 of each such portion abut in alignment. For example, FIG. 5A illustrates an example of a guide 509 with a square cross-section sized to receive at a first end—in a particular orientation—a probe portion 510A that includes a probe body 560 with its four optical fibers 550 distributed thereabout at 0 degrees, 90 degrees, 180 degrees, and 270 degrees. Similarly, a second end of the guide 509 would receive—in an aligned orientation—an external instrumentation lead portion 511B that includes an external instrumentation lead body 560 with four optical fibers 550 similarly distributed thereabout at 0 degrees, 90 degrees, 180 degrees, and 270 degrees. The square cross-section of the guide 509 and the four optical fibers 550 is presented for illustrative purposes only; the underlying idea of using a guide 509 that is shaped to fix and align the radial position of the optical fibers 550 can be extended to any number of one or more optical fibers located on a circumferential surface of a body portion. Moreover, the coupler 509 need not be a unitary piece, but could instead be made of two separate sections that are keyed together, if desired.

In certain examples, the guide 509 is part of (or attached to) an interior portion of a coupler housing 505, and may be plastic, metal, or other suitable material. The housing 505 and the guide 509 may be integrally formed, or may instead be assembled from multiple components. In another example, the guide 509 is separate from the housing 505 and is secured in the housing 505, such as by using adhesive or other suitable material, and the guide 509 may be the same or a different material than the housing 505.

In this example, the external instrumentation lead portion 510B and the probe portion 510A may be made from the same optical cable assembly, such as by sawing the optical cable assembly using a thin dicing wheel or circular diamond-edge blade with a diamond edge blade, or by using ultrasonic cutting. The external instrumentation lead 510B portion and the probe 510A portion may be formed from the same optical cable assembly, or formed from different optical cable assemblies. The sawn ends 511A and 511B of the optical fiber 550 may be further polished, such as to remove surface damage or latent saw damage or subsurface defects due to sawing or to produce substantially parallel surfaces to further improve light coupling between probe and external instrumentation lead portions 510A-B.

FIG. 5B is a cross-sectional side view illustrating an example of the connector 500 for an optical imaging device using a guide. In this illustrative example, only two optical fibers 550 are illustrated, but this is for ease in understanding and not by way of limitation. This example includes a center guide 560, fiber claddings 540, optical fibers 550, and a sheath 530 enclosing the optical fibers 550, the center guide 560, and the fiber claddings 540. The fiber cladding 540 may be the same material as the center guide 560, or it may be a different material. Similarly, the sheath 530 may be the same material as the cladding 540 or center guide 560, or it may be a different material. The center guide 560, the cladding 540 and the sheath 530 may be formed at substantially the same time, or they may be formed separately and later assembled to form the optical cable assembly.

The external instrumentation lead portion 510B is positioned inside the housing 505, conforming to the guide 509, and secured to the housing 505, such as by a compression clamp 516 secured to the housing, or by using adhesive or other suitable material. If necessary, a suitable solvent may be used to remove stray adhesive from the sawn ends. The probe portion 510A is positioned in the housing 505, conforming to the guide 509 with the sawn ends 511A and 511B in mechanical contact and in maximum optical alignment to couple light between the ends 511A-B. The probe portion 510A may be secured to the housing 505, such as by a compression clamp 516 that is secured to the housing, or by adhesive or other suitable material. The ends of the optical fiber 550 may use an antireflective surface coating or an index matching fluid between the ends 511A and 511B to improve light coupling between the probe and external instrumentation lead portions 510A-B.

3. Example Using a Lens Such as A GRIN Lens

Figure 6:
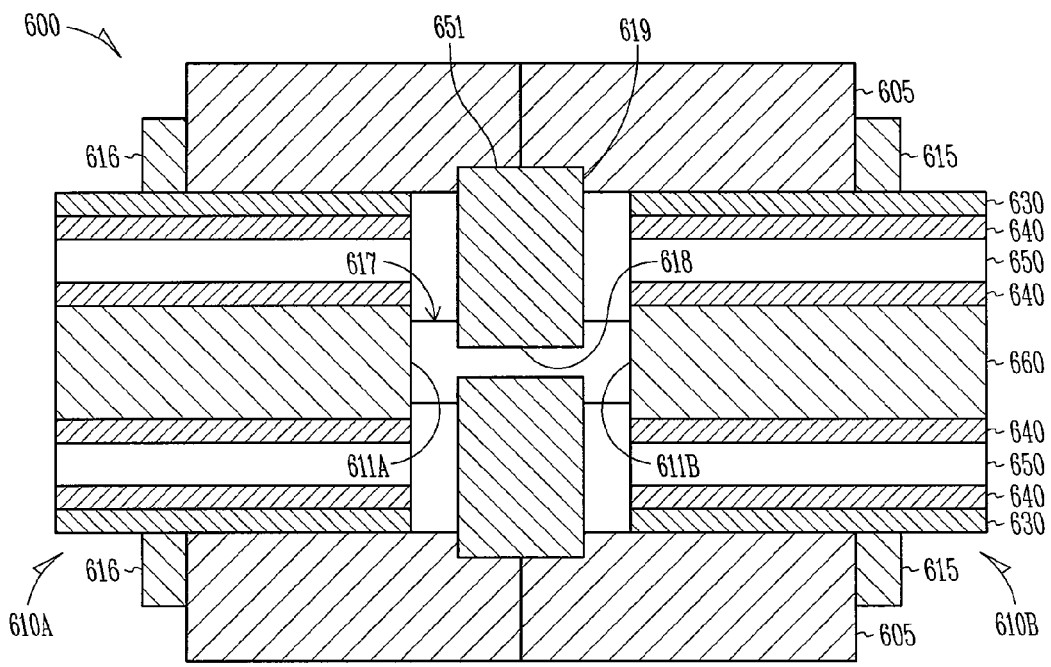
FIG. 6 is a cross-sectional side view illustrating generally one example of a connector using a lens such as a GRIN lens.

FIG. 6 is a cross-sectional side view illustrating one example of a connector 600 for an optical imaging device using a lens such as a graded refractive index (GRIN) lens (or, alternatively, at least one of: a ball lens; a half ball lens; a holographic lens; and a Fresnel lens). In this example, two optical fibers 650 are shown, but this is for ease in understanding and not by way of limitation. A center guide spacer 617 may be used for positioning the GRIN lens 651 with respect to the external instrumentation lead end 611B and the probe end 611A inside the housing 605. In this example, the housing 605 is formed in two separable sections. This allows for positioning of the GRIN lens 651 and the spacer 617. The housing 605 and the spacer 617 may be made from plastic, metal or any other suitable material. In certain examples, the GRIN lens 651 is secured to the spacer 617, such as by adhesive or any other suitable material inside one or more spacer slots 618. The spacer slots 618 are cut or otherwise formed from the spacer 617 to accept a portion of one or more GRIN lenses 651. In another example, the GRIN lens 651 may be positioned partially within the spacer slot 618 without using an adhesive. Similarly, the GRIN lens 651 may also be positioned inside a housing slot 619 cut from housing 605 that is sized to accept one or more GRIN lenses. GRIN lens may be further secured by adhesive or other suitable material or may be positioned inside slot 619 without adhesive.

In this example, the external instrumentation lead portion 610B is secured to the housing 605 such that the external instrumentation lead portion 610B is in contact with a first end of the spacer 617, such as by using a compression clamp 615 that is secured to the housing, or by using adhesive or other suitable technique. The probe portion 610A is inserted into the housing 605 such that the end 611A of the probe portion 610A is in contact with a second end of the spacer 617. The probe portion 610A can be secured to the housing 605 using a compression clamp 616, which is secured to the housing 605, or by using an adhesive or other suitable material. The spacer 617 is typically sized for positioning ends of the optical fibers 650 to obtain increased or maximum light coupling between probe and external instrumentation lead portions 610A-B by the GRIN lens 651 when the center body 660 of the probe and external instrumentation lead ends 611A and 611B, respectively, are in contact with the spacer 617. The ends of the optical fibers 650 may use antireflective surface coatings or an index matching fluid between ends 611A and 611B of respective probe and external instrumentation lead portions 610A-B. This will improve light coupling between the probe and external instrumentation lead portions 610A-B.

Figure 7:
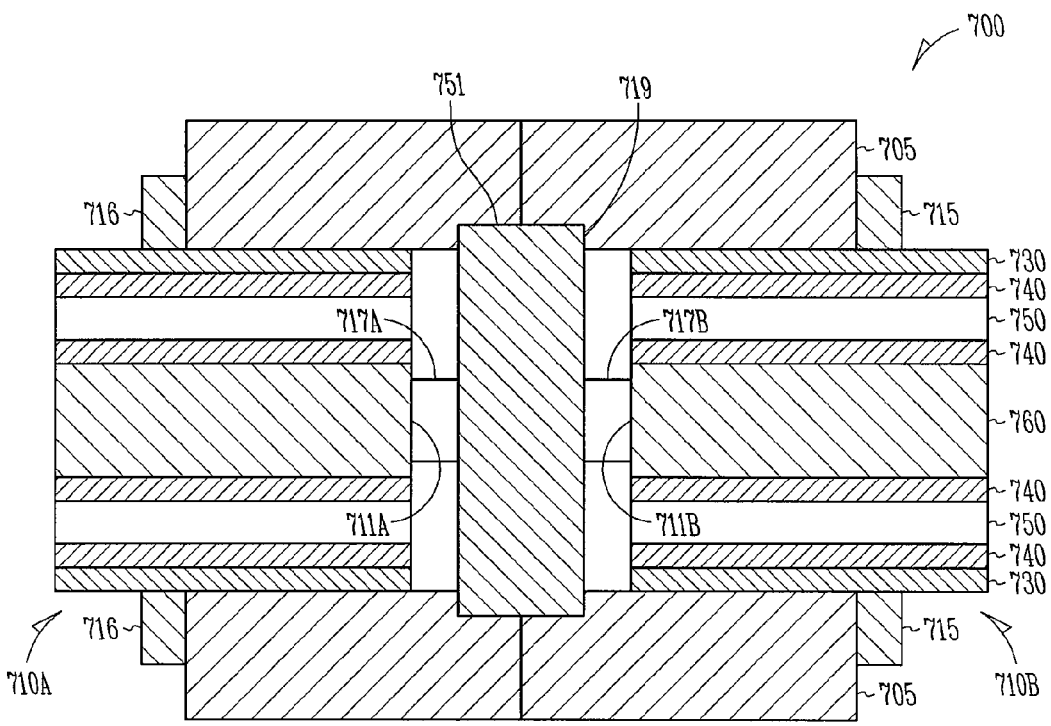
FIG. 7 is a cross-sectional side view illustrating generally one example of a connector using a monolithic GRIN lens.
Figure 10:
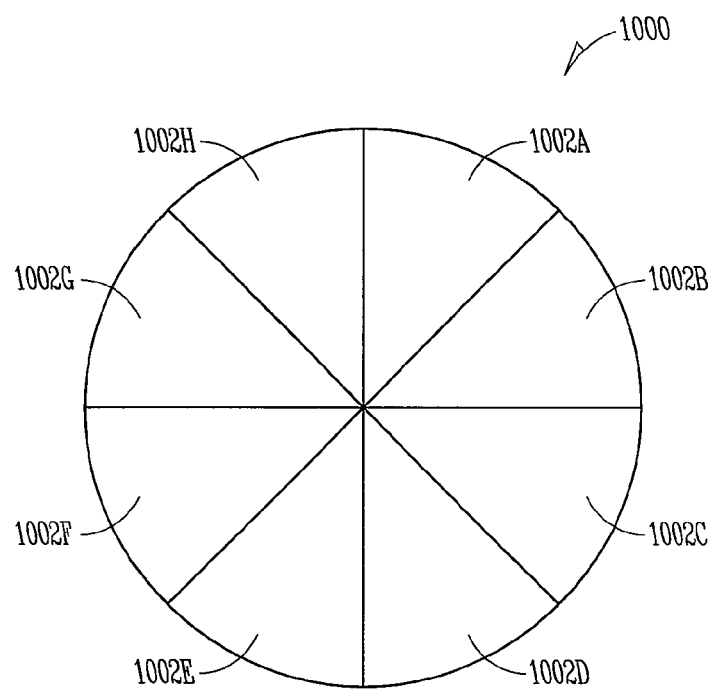
FIG. 10 is an end view illustrating generally one example of a monolithic grin lens having multiple radially partitioned refractive regions.

FIG. 7 is a cross-sectional side view illustrating an example of a connector 700 using an integrated or monolithic GRIN lens 751, 1000 with multiple radial partitioned refractive index regions such as 1002A-H as shown in FIG. 10 (for the case of eight optical fibers 750). In the example of FIG. 7, two optical fibers 750 are shown, but this is for ease in understanding, and not by way of limitation. FIG. 7 shows center guide spacers 717A-B are used for positioning, inside a housing 705, the GRIN lens 751 with respect to the ends 711A-B of the probe and external instrumentation portions 710A-B, respectively. In certain examples, the housing 705 is provided in two separatable sections for easier positioning of the GRIN lens 751 and the spacers 717A-B. The housing 705 may be plastic, metal, or other suitable material. The spacers 717A-B may be plastic, metal, or other suitable material. In certain examples, the spacers 717A-B are secured to the GRIN lens 751, such as by adhesive or other suitable material positioned inside a housing slot 719 cut from the housing 705 and sized to accept the GRIN lens 751. The GRIN lens 751 may be secured to the housing 705, such as by adhesive or other suitable material, or may be positioned inside the slot 719 without using such adhesive In another example, the spacers 717A-B are secured to the center body portions 760A-B, respectively, such as by adhesive or other suitable material, and the GRIN lens 751 is secured to the housing 705.

In the example of FIG. 7, the external instrumentation lead portion 710B is positioned in contact with the spacer 717B at the external instrumentation lead end 711B and secured to the housing 705, such as by a compression clamp 715, or by using adhesive or other suitable material. The probe portion 710A is inserted into the housing 705 such that the end 711A of the probe portion 710 is in contact with the spacer 717A. The probe portion 710 is then secured to the housing 705, such as by the compression clamp 716, or by using an adhesive or other suitable material. In certain examples, the spacers 717A-B are sized for positioning the sawn ends 711A-B to obtain increased or maximum light coupling between probe and external instrumentation lead portions 710A-B by the GRIN lens 751 when the center body 760 of the ends 711A-B are in contact with respective spacers 717A-B. The ends of the optical fibers 750 may use an antireflective surface coating or an index matching fluid between ends 711A-B to improve light coupling between the probe and external instrumentation lead portions 710A-B.

Figure 8A:
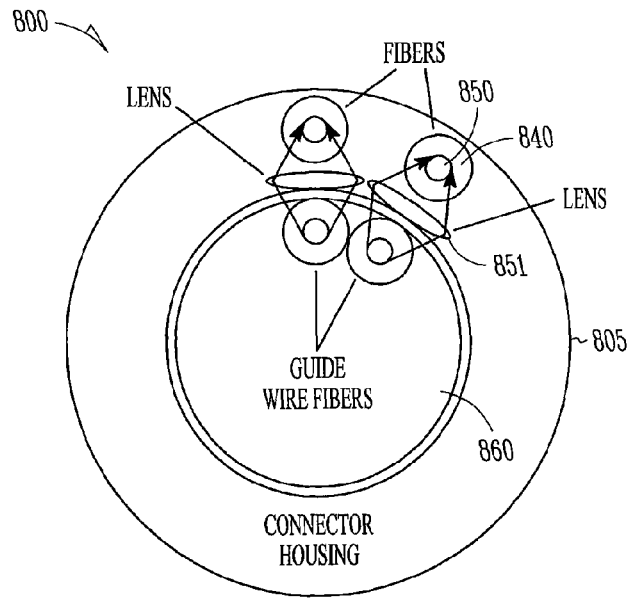
FIG. 8A is a cross-sectional end view illustrating generally one example of a connector using blazed fiber Bragg gratings.
Figure 8B:
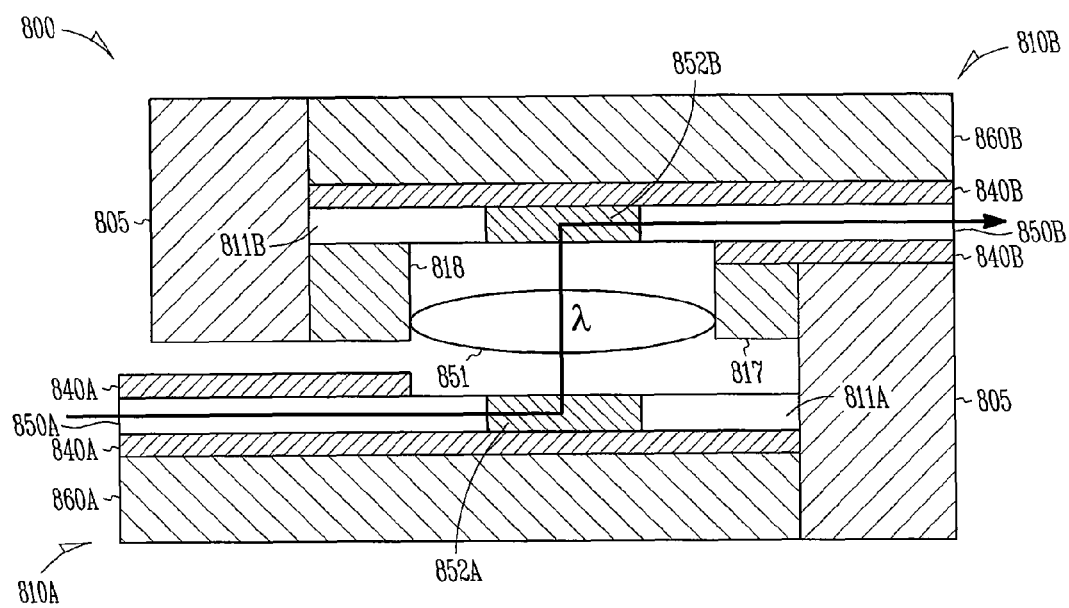
FIG. 8B is a cross-sectional side view illustrating generally one example of a connector using blazed fiber Bragg gratings.

4. Example of a Aligning Optical Imaging Catheter with Blazed Fiber Bragg Gratings FIGS. 8A and 8B are respective cross-sectional end and side views illustrating an example of a connector 800 using at least one lens 851 that is positioned between a pair of blazed fiber Bragg gratings (FBGs). In the example of FIG. 8A, two pairs of optical fibers 850 are shown, but this is for ease in understanding, and not by way of limitation. The optical fibers 850 are concentrically located along the probe and external instrumentation lead portions 810A and 810B, respectively. In certain examples, the probe portion 810A is sized to allow for insertion over the external instrumentation lead portion 810B at ends 811A and 811B. In other examples, the probe portion 810A sized to allow for insertion inside the external instrumentation lead portion 810B. The lens 851 is sized and positioned by one or more lens mounts, such as the lens mounts 817 and 818, to couple light between the probe and the external instrumentation lead portions 810A-B when blazed FBGs 852A-B are aligned.

FIG. 8B is a cross-sectional side view further illustrating this example of a portions of a connector 800 using the lens 851 located between pairs of blazed FBGs. In the example of FIG. 8B, one pair of optical fibers 850 is shown, but this is for ease in understanding, and not by way of limitation. FIG. 8B illustrates a blazed FBG 852B that is patterned into the optical fiber 850B near the end 811B of the external instrumentation lead portion 810B. The external instrumentation lead portion 810B is secured to the housing 805, such as by using a compression clamp that is secured to the housing 805, or by using adhesive or other suitable material. In this example, the lens mounts 817 and 818 are secured to the lead portion 810B near the blazed FBG 852B. The lens mounts 817 and 818 are sized to accept the lens 851 to couple light between the FBGs 852A-B. The lens mount 817 may be configured as a stop for the probe portion 810A. In one example, the lens mounts 817 and 818 are annular rings secured to the inner surface of the external instrumentation lead portion 810B. In another example, the lens mount 818 is shaped as a cap that is secured to the external instrumentation lead portion 810B at its end 811B. In certain examples, the probe portion 810A is positioned inside the lead portion 810B against a stop portion of the lens mount 817. This aligns the FBGs 852A-B for coupling light between the FBGs 852A-B by the lens 851. The probe portion 810A is secured to the housing 805, such as by a compression clamp that is attached to the housing 805, as discussed above, or by using adhesive or other suitable material. The end 811A of the probe portion 810A may otherwise be secured to the stop portion of the lens mount 817, such as by using an plug and receptacle arrangement. In an example in which the probe portion 810A is sized to allow for its insertion over the external instrumentation lead portion 810B, the lens mounts 817 and 818 can be secured to the probe portion 810A, and may be configured as annular rings or as an end cap as shown at 818. The lens mounts 817 and 818 may be metal, plastic, or other suitable material. The lens 851 may use an antireflective surface coating to improve light coupling between blazed FBGs.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, various features may be grouped together to streamline the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus the following claims are hereby incorporated into the Detailed Description, with each claim standing on its own as a separate embodiment.

What is claimed is:

1. An apparatus comprising:
an optical coupler, the coupler comprising a first central body and a plurality of first optical fibers disposed about and extending longitudinally along the first central body, the first central body and the plurality of first optical fibers providing a first commonly beveled end;
wherein the first optical fibers extend away from the first beveled end, the coupler configured to accept an elongated member configured for imaging within an object, the elongated member including a second central body and a plurality of second optical fibers disposed about and extending longitudinally along the second central body, the elongated member having a second commonly beveled end;

wherein the coupler and the elongated member are configured to permit an end-user to insert a beveled end of the elongated member into the coupler, with the elongated member extending away from the second beveled end and the coupler, such that the second beveled end of the elongated member butts against and mates in end-user-provided contacting self-alignment to the first beveled end to couple light between the plurality of the first optical fibers and the contacting self-aligned plurality of the second optical fibers of the elongated member; and wherein the pluralities of the first and second optical fibers are cut, at their respective beveled ends, from a single optical fiber assembly comprising a central body and a plurality of optical fibers disposed about the central body, to permit the end-user-provided contacting self-alignment, wherein the plurality of first optical fibers are disposed about the central body in an encapsulation placement, wherein the encapsulation placement permits relative spatial variations in the placement of the first optical fibers along a length of the optical fiber assembly according to equipment or process variation of the encapsulation.

2. The apparatus of claim 1, further comprising the elongated member configured for imaging within an object, the elongated member including a second central body and a plurality of second optical fibers disposed about and extending longitudinally along the second central body, the elongated member having a second commonly beveled end.

3. The apparatus of claim 2, wherein the elongated member comprises a second commonly beveled end forming a common second plane extending obliquely through both the second central body and the plurality of second optical fibers; and wherein the first central body and the plurality of first optical fibers provide a first commonly beveled end forming a common first plane extending obliquely through both the first central body and the first optical fibers.

4. The apparatus of claim 2, in which the elongated member includes proximal and distal ends and comprises at least one acousto-optical transducer at or near the distal end.

5. The apparatus of claim 1, in which the encapsulation comprises a plastic matrix.

6. The apparatus of claim 1, in which the coupler comprises a housing comprising first and second openings.

7. The apparatus of claim 6, wherein the housing includes a view port positioned to permit receiving light from the beveled end of at least one of the first and second optical fibers.

8. An apparatus comprising:

an optical coupler, the coupler comprising a first central body having a continuously smooth cylindrical outer circumference and a plurality of first optical fibers disposed about the smooth cylindrical outer circumference of the first central body and extending longitudinally along the first central body, the first central body and the plurality of first optical fibers providing a first commonly beveled end;

wherein the first optical fibers extend away from the first beveled end, the coupler configured to accept an elongated member configured for imaging within an object, the elongated member including a second central body and a plurality of second optical fibers disposed about and extending longitudinally along the second central body, the elongated member having a second commonly beveled end;

wherein the coupler and the elongated member are configured to permit an end-user to insert a beveled end of the elongated member into the coupler, with the elongated member extending away from the second beveled end and the coupler, such that the second beveled end butts against and mates in end-user-provided contacting self-alignment to the first beveled end to couple light between the plurality of the first optical fibers and the contacting self-aligned plurality of the second optical fibers of the elongated member; and wherein the pluralities of the first and second optical fibers are cut, at their respective beveled ends, from a single optical fiber assembly comprising a central body and a plurality of optical fibers disposed about the central body, to permit the end-user-provided contacting self-alignment.

9. The apparatus of claim 8, further comprising the elongated member configured for imaging within an object, the elongated member including a second central body and a plurality of second optical fibers disposed about and extending longitudinally along the second central body, the elongated member having a second commonly beveled end.

10. The apparatus of claim 9, wherein the elongated member comprises a second commonly beveled end forming a common second plane extending obliquely through both the second central body and the plurality of second optical fibers; and wherein the first central body and the plurality of first optical fibers provide a first commonly beveled end forming a common first plane extending obliquely through both the first central body and the first optical fibers.

11. The apparatus of claim 8, in which the elongated member includes proximal and distal ends and comprises at least one acousto-optical transducer at or near the distal end.

12. The apparatus of claim 8, wherein the plurality of first optical fibers are disposed about the central body in an encapsulation placement.

13. The apparatus of claim 12, wherein the encapsulation placement permits relative spatial variations in the placement of the first optical fibers along a length of the optical fiber assembly according to equipment or process variation of the encapsulation.

14. The apparatus of claim 13, wherein the encapsulation comprises a plastic matrix.

15. The apparatus of claim 8, in which the coupler comprises a housing comprising first and second openings.

16. The apparatus of claim 15, wherein the housing includes a view port positioned to permit receiving light from the beveled end of at least one of the first and second optical fibers.

17. An apparatus comprising:

an optical coupler, the coupler comprising a first central body and a plurality of first optical fibers disposed about and extending longitudinally along the first central body in an encapsulation placement, the first central body and the plurality of first optical fibers providing a first commonly beveled end;

wherein the first optical fibers extend away from the first beveled end, the coupler configured to accept an elongated member configured for imaging within an object, the elongated member including a second central body and a plurality of second optical fibers disposed about and extending longitudinally along the second central body, the elongated member having a second commonly beveled end;

wherein the coupler and the elongated member are configured to permit an end-user to insert a beveled end of the elongated member into the coupler, with the elongated member extending away from the second beveled end and the coupler, such that the second beveled end butts against and mates in end-user-provided contacting self-alignment to the first beveled end to couple light between the plurality of the first optical fibers and the contacting self-aligned plurality of the second optical fibers of the elongated member; and wherein the pluralities of the first and second optical fibers are cut, at their respective beveled ends, from a single optical fiber assembly comprising a central body and a plurality of optical fibers disposed about the central body, to permit the end-user-provided contacting self-alignment.

18. The apparatus of claim 17, wherein the encapsulation placement permits relative spatial variations in the placement of the first optical fibers along a length of the optical fiber assembly according to equipment or process variation of the encapsulation.

19. The apparatus of claim 18, wherein the encapsulation comprises a plastic matrix.

20. The apparatus of claim 17, in which the coupler comprises a housing comprising first and second openings.

21. The apparatus of claim 20, wherein the housing includes a view port positioned to permit receiving light from the beveled end of at least one of the first and second optical fibers.

* * * * *

UNITED STATES PATENT AND TRADEMARK OFFICE
CERTIFICATE OF CORRECTION

| | |
|---|---|
| PATENT NO. | : 7,881,573 B2 |
| APPLICATION NO. | : 12/572511 |
| DATED | : February 1, 2011 |
| INVENTOR(S) | : Michael J. Eberle et al. |

Page 1 of 1

It is certified that error appears in the above-identified patent and that said Letters Patent is hereby corrected as shown below:

On Title Page 3, Item (56), under "Other Publications", in column 2, line 50, delete "Standford" and insert -- Stanford --, therefor.

On Title Page 4, Item (56), under "Other Publications", in column 1, line 27, delete "anErbium" and insert -- an Erbium --, therefor.

On Title Page 4, Item (56), under "Other Publications", in column 2, line 1, delete "Reconition" and insert -- Recognition --, therefor.

On Title Page 4, Item (56), under "Other Publications", in column 2, line 5, delete "wen" and insert -- web --, therefor.

On Title Page 4, Item (56), under "Other Publications", in column 2, line 15, delete "Clenical" and insert -- Clinical --, therefor.

On Title Page 4, Item (56), under "Other Publications", in column 2, line 43, delete "Thermagraphy" and insert -- Thermography --, therefor.

On Title Page 4, Item (56), under "Other Publications", in column 2, line 44, delete "Plagues" and insert -- Plaques --, therefor.

In column 5, line 33, delete "10A" and insert -- 110A --, therefor.

In column 10, line 10, delete "611 B" and insert -- 611B --, therefor.

In column 10, line 61, delete "separatable" and insert -- separable --, therefor.

Signed and Sealed this
Nineteenth Day of April, 2011

David J. Kappos
*Director of the United States Patent and Trademark Office*